United States Patent [19]

Umezawa et al.

[11] Patent Number: 4,663,342

[45] Date of Patent: May 5, 1987

[54] PHARMACEUTICAL COMPOSITION AND METHOD FOR IMMUNOPOTENTIATION

[75] Inventors: Hamao Umezawa, Tokyo; Takaaki Aoyagi, Fujisawa; Tomio Takeuchi, Tokyo; Masa Hamada, Tokyo; Masaaki Ishizuka, Tokyo, all of Japan

[73] Assignee: Zaidan Hojin Biseibutsu Kagaku Kenkyu Kai, Tokyo, Japan

[21] Appl. No.: 749,456

[22] Filed: Jun. 27, 1985

[30] Foreign Application Priority Data

Jul. 3, 1984 [JP] Japan .................................. 59-136462

[51] Int. Cl.⁴ ............................................. A61K 31/40
[52] U.S. Cl. ........................................................ 514/423
[58] Field of Search .......................................... 514/423

[56] References Cited

U.S. PATENT DOCUMENTS 3,240,787  3/1966  Singh et al. ........................ 435/121

OTHER PUBLICATIONS

Glasby, Encyclopaedia of Antibiotics, John Wiley & Sons, N.Y., N.Y., Aug. 24, 1977, p. 17.

Primary Examiner—Jerome D. Goldberg
Attorney, Agent, or Firm—Larson and Taylor

[57] ABSTRACT

A compound of the formula (I)

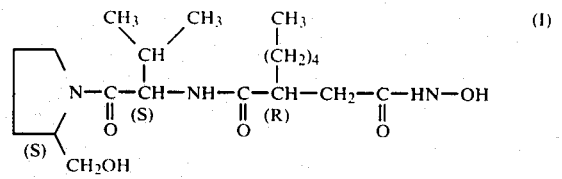

which is identified as an actinonin has now been found to potentiate the immune response in animals bearing Ascites Sarcoma 180 tumor cells.

2 Claims, No Drawings

PHARMACEUTICAL COMPOSITION AND METHOD FOR IMMUNOPOTENTIATION

SUMMARY OF THE INVENTION

This invention also relates to a method for potentiating or stimulating the immune response in a living animal bearing Ascites Sarcoma 180 tumor cells.

BACKGROUND OF THE INVENTION

It is known that a Streptomyces strain (NCIB 8845) or (ATCC No. 14,903) produces an antibiotic named Actinonin which exhibits antibacterial activity against gram-positive bacteria (U.S. Pat. No. 3,240,787). Some substances useful as the host defence stimulator or immunopotentiator are known, but there remains a need for a more effective agent useful for therapeutic, immunological treatment of in living animals bearing Ascites Sarcoma 180 tumor cells.

A further object of this invention is to provide a method for potentiating or stimulating the immune response in a living animal bearing Ascites Sarcoma 180 tumor cells. Other objects of this invention will be clear from the following descriptions.

From extensive researches, we, the present inventors, have found that such a substance which has an activity inhibitory to the enzymatic activity of an enzyme existing on the surfaces of organism cells have immunomodulating activities. And we have made researches in an attempt to find out such biologically active substances which are capable of enhancing the cellular or cell-mediated immunity, and as a result, we have now found that a substance which is produced by a microorganism having our laboratory designation Strain MG848-hF6 (an actinomycetes strain as isolated by us and stored in our laboratorys, the Institute of Microbial Chemistry, of Kami-Ohsaki, Shinagawa-ku, Tokyo, Japan) and which has been recovered by us and identified as an actinonin and given the following chemical structure:

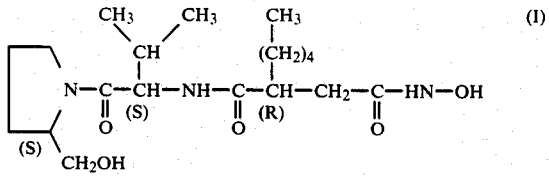

and a salt thereof have a remarkably high immunopotentiating acitivity in animals bearing Ascites Sarcoma 180 tumor cells. The actinonin obtained by us is in the form of colorless needles which show a melting point of 148°–149° C. and give a specific optical rotation $[\alpha]_D^{20} -50°$ (c 2, ethanol). Based on this finding, we have accomplished this invention.

Actinonin as disclosed in literatures is known as a compound having antibacterial activity (see "I.A.M. Symposia on Microbiology" No. 6, "Chemistry of Microbial Product" pages 204–214 (1964) and U.S. Pat. No. 3,240,787). In these literatures, it is disclosed that actinonin has the following formula

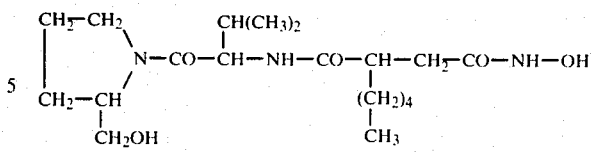

and shows physico-chemical properties, such as a melting point of 148°–149° C. and an $[\alpha]_D^{20} -53.9°$ in ethanol and $-65.0°$ in water and that this actinonin exhibits an antibacterial activity. However, only through our recent researches, it has firstly been discovered by us that the compound of the formula (I) as obtained by us and identified as an actinonin exhibits pharmacological activities, particularly the activity of potentiating the cellular or cell-mediated immunity, namely the activity of enhancing or stimulating the immune response in a living animal bearing Ascites Sarcoma 180 tumor cells and is useful as a host defence stimulator for enhancing the immune response in a living animal bearing Ascites Sarcoma 180 tumor cells.

DETAILED DESCRIPTION OF THE INVENTION

According to a first aspect of this invention, therefore, there is provided a pharmaceutical composition, useful as immunopotentiator in living animals bearing Ascites Sarcoma 180 tumor cells, which comprises as the active ingredient an actinonin compound of the formula

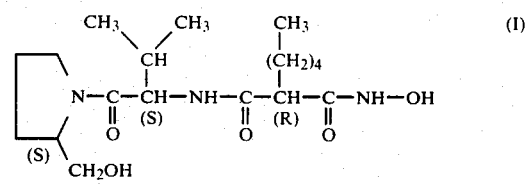

or a pharmaceutically acceptable acid addition salt thereof in an immunopotentiatingly effective amount thereof, in combination with a pharmaceutically acceptable carrier for the active ingredient.

According to a second aspect of this invention, there is provided a method of potentiating the immune response in a living animal bearing Ascites Sarcoma 180 tumor cells, which comprises administering to said animal an immunopotentiatingly effective amount of an actinonin of the above formula (I) or a pharmaceutically acceptable acid addition salt thereof.

The pharmaceutically acceptable acid addition salt of the actinonin as above includes a salt with a known pharmaceutically acceptable inorganic acid such as hydrochloric acid, sulfuric acid, phosphoric acid and the like, or a known pharmaceutically acceptable organic acid such as acetic acid, propionic acid, citric acid, oxalic acid and the like.

The pharmaceutically acceptable carrier available in this invention may be a conventional liquid one such as water, ethanol, aqueous ethanol, or a conventional solid one such as starch, casein, talc and the like.

We have recovered and obtained the actinonin of the formula (I) from the culture broth of the actinomycetes strain MG848-hF6 where the actinonin has been produced and accumulated therein. Normally, this actinonin can be recovered in a good yield by a method comprising filtering the culture broth of the actinomycetes strain MG848-hF6, making the actinonin present in the culture broth filtrate to be adsorbed by an adsorbent, and releasing it from the adsorbent according to a conventional technique for recovery of antibiotics.

The biological activities of actinonin of the formula (I) are described below, with reference to the following Test Examples.

TEST EXAMPLE 1

Effect of actinonin on cellular immunity in normal mice (i) Test Procedure

Effect of actinonin on the cellular immunity was investigated by measuring the Delayed Type Hypersensitivity (D.T.H.) (see P. H. Lagrange, G. B. Mackaness and T. E. Miller: "J. Exp. Med.", 139, 1529–1539 (1974)) using mice immunized with sheep red blood cells (SRBC) as the antigen inoculated to the footpad of the mice.

Thus, $10^8$ SRBC suspended in 0.05 ml of physiological saline was inoculated by subcutaneous injection into a subdermal site of a hind footpad of $CDF_1$ mice (6 mice per group, female, 8-weeks old) to make immunization. At the time of this immunization, an aqueous solution containing 5 mg/kg, 0.5 mg/kg, 0.05 mg/kg or 0.005 mg/kg of actinonin was administered intraperitoneally at a single dose to each test mice. 4 Days after the immunization, $10^8$ SRBC in 0.05 ml of physiological saline were injected subcutaneously into the other hind footpad of the test mice for secondary challenge of the D.T.H. response. 24 Hours after the challenge, the thickness (in mm) of the hind footpad having received the challenge of SRBC was measured with vernier caliper. At the same time, the thickness of footpad of control mice which had received the injection of the SRBC and physiological saline without the administration of the test compound was also measured in each mouse. The increase in footpad thickness of the animals treated was calculated by the following equation:

Increase in footpad thickness =

(Thickness of the footpad having received the challenge) −

(Thickness of the footpad having not received the challenge)

The effect of actinonin on the DTH response was evaluated by the following equation:

$$T/C\ (\%) = \frac{\text{Mean value } (T) \text{ of the increase in footpad thickness in mice treated with actinonin}}{\text{Mean value } (C) \text{ of the increase in footpad thickness in mice untreated}} \times 100$$

Therefore, the assumption was taken here that the value for the control mice (untreated) was evaluated to be 100%.

In this way, the cell-mediated immunity potentiating effect of the test compound was evaluated. For comparison purpose, bestatin was also tested in the same manner as above. The test results are shown in the following Table 1.

(ii) Test results

TABLE 1

| Test Compound | Dose (mg/kg) | Increase in footpad thickness (× 0.1 mm) | T/C (%) |
| --- | --- | --- | --- |
| Actinonin | 5 | 11.9 ± 1.44 | 138* |
| Actinonin | 0.5 | 11.4 ± 1.80 | 133* |
| Actinonin | 0.05 | 10.4 ± 1.40 | 121 |
| Actinonin | 0.005 | 9.2 ± 1.15 | 107 |
| Bestatin (comparative) | 0.5 | 12.8 ± 1.47 | 149* |
| Control | | 8.6 ± 1.78 | 100 |

*Significantly different from the increase in footpad thickness of the control ($P < 0.05$)

As will be clear from the above, actinonin at doses of 5 mg/kg and 0.5 mg/kg increased significantly the footpad thickness of mice, giving the values of 138 and 133%, respectively, but the effect of actinonin was slightly lower than the comparative drug, bestatin given at a dose of 0.5 mg/kg.

TEST EXAMPLE 2

Effect of actinonin on the cellular immunity in tumor-bearing mice with immunization by picryl chloride as hapten antigen and challenge with picryl chloride In mice bearing Ascites Sarcoma 180 tumor, the effect of actinonin on the D.T.H. response to picryl chloride was investigated.

(i) Testing procedure $10^6$ Cells of Ascites Sarcoma 180 were transplanted intraperitoneally into $CDF_1$ mice (12-week-old, female, 5 mice per group). The day of this transplantation was designated as Day 0. On Day 1, the left ear of the mice was immunized with 20 μl of a solution of 1% picryl chloride in ethanol which had been absorbed to a mass of absorbent cotton (cut to 10 mm × 5 mm × 1 mm in size). Then, 5.0 mg/kg, 0.5 mg/kg, 0.05 mg/kg or 0.005 mg/kg of actinonin dissolved in physiological saline was orally administered once daily from Day 1 to Day 8, except that on Days 5 and 6 the test compound was not administered. During this period of Day 1 to Day 8, the control group of mice (untreated) was given physiological saline only. On day 8, the right ear was challenged with 20 μl of a 1% olive oil solution of picryl chloride which was absorbed to an absorbent cotton mass cut to a size of 10 mm × 5 mm × 1 mm. Twenty-four hours after the challenge, the thickness of the ear was measured with a dial gauge.

On the other hand, the control animals (untreated) were challenged on Day 8 with picryl chloride and physiological saline in accordance with the same procedure, but without having been treated with the test compound, and the thickness of the ear of the control animals was measured in the same way. The increase in the thickness of ear for the control group of mice was evaluated to be 100%.

The increase (T) in the thickness of the ear for the group of mice treated with the test compound was compared with that (C) for the control group of mice to evaluate the rate (T/C, %) of the increase in the thickness of the ear, whereby the cellular immunity-potentiating activity of the compound under test was estimated.

(ii) Test Results

TABLE 2

| Test compound | Dose (mg/kg) | Increase in ear thickness (× $10^{-3}$ cm) | T/C (%) |
| --- | --- | --- | --- |
| Actinonin | 5 | 4.60 ± 1.19 | 94.8 |

TABLE 2-continued

| Test compound | Dose (mg/kg) | Increase in ear thickness ($\times 10^{-3}$ cm) | T/C (%) |
| --- | --- | --- | --- |
|  | 0.5 | 7.08 ± 1.66* | 146.0 |
|  | 0.05 | 6.80 ± 0.84* | 140.2 |
|  | 0.005 | 4.70 ± 0.67 | 96.9 |
| Bestatin | 0.5 | 6.75 ± 1.51* | 139.2 |
| Control |  | 4.85 ± 0.58 | 100 |

*$P < 0.05$

The results of Table 2 have revealed that actinonin exhibits a significant activity of potentiating the cellular immunity as high as that of the comparative drug, bestatin.

In view of the above test results altogether, it is clear that the actinonin compound of the formula (I) potentiates the Ascites Sarcoma 180 cell-mediated immunity not only in normal, healthy animals but also in animals having a cellular immunity as depressed by the tumor, and said compound exhibits a host-mediated anti-tumor effect.

Acute toxicity tests in mice by intravenous injection have shown that no deaths are caused by the actinonin compound of the formula (I) at an i.v. dosage of 400 mg/kg. The actinonin compound of the formula (I) is hence a safe substance. As described above, the actinonin compound (I) as used according to this invention augments the immunity and exhibit a host-mediated carcinostatic effect when administered singly. The actinonin compound of the formula (I) is therefore useful as an immunopotentiator and anti-tumor immunomodulator or as adjuvants to various chemotherapeutic agents for use in the treatment of carcinomas.

The pharmaceutical composition according to this invention may comprise a safe and effective amount of at least one of the actinonin compound of the formula (I) and a pharmaceutically acceptable salt thereof, in admixture with a pharmaceutically acceptable carrier.

The drugs containing the actinonin compound as active ingredients can be prepared by blending the actinonin or a pharmaceutically acceptable salt thereof with a conventional carrier, and if desired, further with various chemotherapeutic agents.

The actinonin compound or drugs according to this invention may be administered as oral preparations, injections or rectal suppositories. Lyophilized injections can be prepared by admixing pH-adjustors, buffers, stabilizers and excipients with the active ingredient compounds, and then freeze-drying the mixtures in a conventional manner. Injections for subcutaneous, intramuscular or intravenous administration can be prepared by admixing pH-adjustors, buffers, stabilizers, isotonizers and local anesthetics with the active ingredient compounds, and then formulating the mixture by known procedures.

For the preparation of oral solids, the active ingredient compound is admixed with excipients, if desired, together with binders, disintegrators, lubricants, colorants, taste correctives and odor correctives, whereafter the mixture are formed into tablets, coated tablets, granules, powders and capsules by conventional methods.

For the preparation of oral liquids, the active ingredient compound may be admixed with taste-correctives, buffers, stabilizers and odor correctives and then the mixtures are made into syrups and dry syrups by conventional methods.

To prepare rectal suppositories, the active ingredient compound may be admixed with excipient, if desired, together with surfactant, and the mixture is prepared into suppositories by conventional techniques. The dose of the actinonin compound to be administered to animals may be varied depending on symptoms of the disease, but the usual dosage of the actinonin is 1 mg to 200 mg for adult once daily. When concomitant therapy with other chemotherapeutic agents for carcinomas or other immunopotentiators is to be attempted, the actinonin compound in said dose range may be administered in association with these other drugs in their usual doses.

The production of the actinonin compound will be described with reference to the following Example.

EXAMPLE

The actinonin-producing microorganism, Strain MG848-hF6 (as stored in our laboratory) was cultivated in a culture medium in a manner known for the cultivation of actinomycetes, and the culture broth obtained was filtered. The resulting broth filtrate was passed through a column of an adsorbent resin, Amberlite XAD-4 (a product of Rohm & Haas Co., U.S.A.) of which the volume amounted to 1/10th of the volume of the broth filtrate, so that the actinonin was adsorbed by the Amberlite XAD-4 resin. The Amberlite XAD-4 resin in the column was washed with water and then eluted with a solution of 80% methanol in water. The eluate in the aqueous 80% methanol was concentrated to dryness under reduced pressure to give a crude powder (I) containing the actinonin. This crude powder (I) was subjected to a column chromatography on silanized silica gel with being gradiently eluted with a buffered solution containing 1% citric acid and 2% potassium acetate (pH 4.9) and a varying amount of from 0% to 80% of acetonitrile. The eluate was collected in fractions, and the active fractions containing the actinonin were obtained, combined together and concentrated under reduced pressure to a 1/10th volume of the original volume. The concentrated solution obtained was passed through a column of an adsorbent resin, Amberlite XAD-4 for the de-salting purpose. The Amberlite XAD-4 resin in this column was washed with water and then eluted with a solution of 80% methanol in water, followed by concentrating the eluate to dryness under reduced pressure to afford a crude powder (II) containing the actinonin. This crude powder (II) was then subjected to a chromatography on silica gel as eluted with chloroform-methanol (95:5). The eluate was collected in fractions, and the active fractions containing the actinonin were obtained and combined together. The combined active fractions were concentrated to dryness under reduced pressure to give a pure product of the actinonin as isolated. Recrystallization of this product gave colorless needles of the actinonin. mp. 148°-149° C.

Assay of the actinonin was conducted during the step of the cultivation of the actinonin-producing microorganism and the step of the purification to trace the amounts of the actinonin. The assaying method employed comprised determining the potency of the actinonin inhibitory to an aminopeptidase M in a manner described below.

Thus, 0.5 ml of 0.1M Tris-hydrochloride buffer solution (pH 7.0) and 0.2 ml of a solution of an actinonin specimen were added to 0.25 ml of a substrate solution of 0.002M leucine-$\beta$-naphthylamide (a product of Bachem Feinchemikalien AG.). The mixture obtained was heated at 37° C. for 3 minutes, and to the heated mixture was added 50 μl of a solution of an aminopeptidase M (extracted from swine kidney, a product of Boehringer Mannheim Co.). The resulting mixed solutions were incubated at 27° C. for 30 minutes, and to the resultant reaction solution was added 1 ml of a 1.0M acetate buffer solution (pH 4.2) containing 1 mg/ml of Fast Garnet GBC (o-aminoazotoluene diazonium salt) and 10% of a surfactant "Tween" 20, to stop the enzymatic reaction. The resulting reaction solution was allowed to stand at room temperature for 15 minutes, and then the adsorbance at 525 nm of the reaction solution was measured, with designating the measured value as value (a). Concurrently, measurement was made about the adsorbance at 525 nm of a "control" reaction solution which was obtained from the blank test using the buffer solution only without the solution of actinonin, and the measured value of the absorbance here was designated as value (b). The rate (%) of inhibition to the aminopeptidase M was calculated from an equation $[(b-a)/b] \times 100$. In accordance with this assaying method, a pure product of the actinonin of the formula (I) had a potency that its $IC_{50}$ value, namely the dose of giving 50% inhibition to the aminopeptidase M amounted to 0.4 μg/ml.

What we claim is:

1. A method of potentiating the immune response in a living animal bearing Ascites Sarcoma 180 tumor cells, which comprises administering to the animal an immunopotentiatingly effective amount of actinonin or a pharmaceutically acceptable acid addition salt of actinonin.

2. The method as claimed in claim 1 in which the animal is a mouse.

* * * * *